United States Patent [19]

Newell

[11] 4,374,125

[45] Feb. 15, 1983

[54] HAIR MOISTURIZING COMPOSITIONS

[75] Inventor: Gerald P. Newell, Hanover Park, Ill.

[73] Assignee: Helene Curtis Industries, Inc., Chicago, Ill.

[21] Appl. No.: 912,360

[22] Filed: Jun. 5, 1978

[51] Int. Cl.³ .................... A61K 7/06; A61K 47/00
[52] U.S. Cl. ................................ 424/70; 424/359; 424/362; 424/365
[58] Field of Search ............ 424/DIG. 2, 70, 362, 424/365, 359

[56] References Cited

U.S. PATENT DOCUMENTS

| | | | |
|---|---|---|---|
| 3,235,457 | 2/1966 | Laden | 424/65 |
| 3,450,674 | 6/1969 | Walles | 425/71 |
| 3,683,939 | 8/1972 | Johnsen | 424/70 |
| 3,822,312 | 7/1974 | Sato et al. | 424/70 |
| 3,948,943 | 4/1976 | Eberhardt et al. | 424/65 |
| 4,076,800 | 2/1978 | Marsh et al. | 424/70 |

FOREIGN PATENT DOCUMENTS

| | | | |
|---|---|---|---|
| 44-22440 | 9/1969 | Japan. | |
| 49-27643 | 7/1974 | Japan | 424/70 |
| 51-20639 | 6/1976 | Japan | 424/70 |
| 76-04794 | 11/1976 | Netherlands | 424/70 |

OTHER PUBLICATIONS

Drug & Cosmetic Industry, 84(4) at p. 440(t), (1960), Thomsen.
Amer. Perfumer and Cosmetics, 78(10), pp. 69–72, (1963), Burnett, Proteins in Cosmetics.

*Primary Examiner*—Douglas W. Robinson
*Attorney, Agent, or Firm*—Dressler, Goldsmith, Shore, Sutker & Milnamow, Ltd.

[57] ABSTRACT

An aqueous hair treatment composition for restoring the proper moisture level in initially moisture deficient hair and maintaining the proper moisture level in hair initially having a normal moisture content comprising from about 0.01 to about 1 weight percent of sodium-2-pyrrolidone-5-carboxylate, from about 0.05 to about 5 weight percent of glycerin, and from about 0.05 to about 5.0 weight percent of protein derived from a collagenous source.

9 Claims, No Drawings

HAIR MOISTURIZING COMPOSITIONS

BACKGROUND OF THE INVENTION

This invention relates to compositions for applications to hair and more specifically relates to compositions for restoring a normal moisture level in hair initially having a moisture deficiency and maintaining the normal moisture level in hair initially having a normal moisture content.

The use of hair coloring or bleaching products, permanents, straighteners, blowdryers and exposure to sun, wind, indoor heating, etc. are all drying and damage the hair by robbing it of moisture. Moisture deficient hair is dull, brittle and lifeless.

A number of products have been developed in recent years to improve the condition of hair. While many of the available hair-conditioning compositions improve the sheen, combability and manageability of hair, they do little to restore and maintain the normal moisture content of hair. Thus, there is a need for improved products which can restore and maintain the normal content of hair as well as condition it to improve its sheen, combability and the like. The present invention provides such compositions.

Laden U.S. Pat. No. 3,235,457, issued Feb. 15, 1966, discloses the use of the free acid or the hygroscopic salts of 2-pyrrolidone-5-carboxylic acid, 1-methyl-2-pyrrolidone-5-carboxylic acid and 4-methyl-2-pyrrolidone-5-carboxylic acid as humectants in cosmetic compositions which are to be applied to hair or skin. Laden discloses incorporating the humectants into the cosmetics and other compositions to prevent the products from losing moisture and drying out in storage. Laden further teaches that the humectants must be present in an amount of at least 2 weight percent of such compositions, and preferably from 4 to 10 weight percent. Glycerin is also known to be a humectant.

It has now surprisingly been found that when from about 0.01 to about 1 weight percent of sodium-2-pyrrolidone-5-carboxylate is incorporated into hair treatment compositions such as shampoos, conditioners, and the like, along with glycerin and protein derived from a collagenous source, the moisture level can be restored to moisture deficient hair, and normal moisture content can be maintained in normal hair.

Thus, the present invention provides improved hair compositions which are adapted to restore the normal moisture content to initially moisture deficient hair and maintain normal moisture levels in hair initially having a normal moisture content.

SUMMARY OF THE INVENTION

The compositions of this invention can be shampoos, conditioners, blow-drying lotions, hair sprays and the like which are adapted to restore the normal moisture content to hair initially having a slight to severe moisture deficiency and maintaining normal moisture content in hair initially having a normal moisture level. The compositions comprise from about 0.01 to about 1.0 weight percent of sodium-2-pyrrolidone-5-carboxylate, from about 0.05 to about 5.0 weight percent of glycerin and from about 0.05 to about 5.0 weight percent of protein derived from collagenous sources. Additionally, the compositions include the normal or usual ingredients of such compositions.

Thus, in addition to unique combination of sodium-2-pyrrolidone-5-carboxylate, glycerin and protein, the compositions of this invention may additionally comprise quaternary conditioners, detergents, thickeners, fatty esters, other known quaternary conditioning agents, fragrance solubilizers, etc.

The compositions of this invention are used in concert with each other in a prescribed manner to achieve the desired end result as discussed hereinbelow.

DETAILED DESCRIPTION OF THE PREFERRED EMBODIMENTS

The hair moisturizing compositions of this invention comprise an aqueous dispersion containing from about 0.01 to about 1.0 weight percent, preferably from about 0.05 to about 0.5 weight percent of sodium-2-pyrrolidone-5-carboxylate; from about 0.01 to about 5.0 weight percent, preferably from about 0.1 to about 2.0 weight percent of glycerin and from about 0.01 to about 5.0 weight percent, preferably from about 0.1 to about 2.0 weight percent of protein derived from a collagenous source.

In order to determine whether hair has a normal moisture content, the hair to be tested is dried out in a vacuum oven and accurately weighed. The hair is then allowed to equilibrate at ambient room humidity and reweighed accurately. The increased weight is due to moisture pickup. The percent of moisture remaining is then calculated as follows:

$$\frac{\text{Wt. of hair at a given room humidity} - \text{Wt. of dry hair}}{\text{Wt. of dry hair}} \times 100 = \%$$

Hair having an average of 6.3 weight percent moisture gain is considered as hair having a normal moisture content. Hair having a 5.6 average weight percent moisture gain is considered to be moderately moisture deficient hair and hair having an average moisture content of about 5% or lower is considered as hair having an extreme or severe moisture deficiency.

Depending upon whether the compositions of this invention are formulated as shampoos or as various types of conditioners or setting lotions for initially normal, moderately moisture deficient or severely moisture deficient hair, the compositions of this invention can include other ingredients which are generally used in the particular type of compositions. Thus, for example, if the composition is formulated as a shampoo, it can include from about 5 to about 50% weight percent of a suitable detergent such as sodium lauryl sulfate or a sodium lauryl sulfate containing detergent, i.e., Dynol SAM sold by Richardson Co. alone or together with an amphoteric surface active agent such as the monosodium salt of N-lauryliminodipropionic acid, i.e. Deriphat 160C sold by General Mills, which can be present in the shampoo in an amount of from about 0.05 to 10 weight percent, preferably 0.1 to about 5 weight percent of the shampoo, and a nonionic detergent such as a coconut diethanolamide, i.e. Ninol 2012 sold by Stepan Chemical Company. In addition, the shampoo compositions of this invention can include foam boosters and stabilizers such as lauryl dimethylamine oxide, i.e. AMMONYX-LO sold by Onyx Chemicals, which can be present in an amount of from about 1 to 15 weight percent, preferably from about 2 to 10 weight percent of the composition. The shampoos can also include chelating agents such as ethylenediaminetetraacetic acid (EDTA) and preservatives such as Methyl Parasept sold by Tenneco Chemical Company, glutaraldehyde, monomethyloldimethyl hydantoin and the like. The shampoo formulations can also include perfuming agents, coloring agents and the like.

The conditioning compositions of this invention can include, in addition to the sodium-2-pyrrolidone-5-carboxylate, glycerin and protein, conditioners such as alkylmethyl bis (polyoxyethylene) quaternary ammonium salt, i.e., Ethoquad O/12 sold by Armak Chemical Company, which can be present in an amount of from about 0.5 to about 5 weight percent, preferably from about 2 to about 4 weight percent; a cationic surface active agent such as cetyltrimethyl ammonium chloride (29% active solution) sold under the trademark Barquat CT-429 sold by Lonza, Inc.; stearic acid, which can be present in an amount of from about 0.5 to about 3 weight percent, preferably 1.0 to 2.0 weight percent; glycerol monostearate, which can be present in an amount of from about 0.5 to about 3.0 weight percent, preferably from about 1 to about 2 weight percent, cetyl alcohol which can be present in an amount of about 0.5 to about 5 weight percent, preferably from about 2.0 to about 3 weight percent; polyethylene glycol polymer of ethylene oxide having an average molecular weight of 3,000–3,700 such as that sold by Union Carbide Chemical Company under the tradename Carbowax 4000 which can also be present in an amount of 0.5–5.0 weight percent, and pantothenyl alcohol, which can be present in an amount of 0.05 to 5 weight percent of the composition, in addition to perfuming agents, coloring agents and the like.

It will be understood to those skilled in the art that the above ingredients variously serve as conditioning agents, thickeners and opacifiers, anti-static agents and the like. Generally speaking, when the unique combination of humectants and protein are combined with any or all of the above ingredients, the resulting conditioner is referred to herein as a moisture stabilizing conditioner.

If a moisture control setting conditioner is desired, the three principal ingredients can, for example, be combined with denatured ethanol such as SD alcohol 40, generally at about 25 to 35 weight percent of the composition; from about 1 to about 10 weight percent of a film forming resin such as the 80% vinylpyrrolidone-20% dimethylaminoethyl methacrylate copolymer quaternized with diethyl ammonium sulfate such as GAF Quat 734 sold by General Aniline and Film Corporation; from 0.1 to about 2 weight percent of a quaternary anti-static conditioner such as dimethyl difatty ammonium chloride in aqueous isopropanol such as that sold by Ashland Chemical Company under the tradename ADQGEN 432 CG, and a cationic surface active agent such as Ethoquad O/12, identified above. The moisture control setting conditioner can additionally include perfumes and non-ionic surface active agents which also serve as perfume-solubilizers such as a polyoxyalkylene derivative of sorbitan monolaurate, i.e., TWEEN 20 sold by ICI United States, Inc., and coloring agents.

If the hair is to be blown dry or set with hot curlers, a thermal styling protective lotion is provided by combining the protein and two humectants with from about 0.2 to about 10 weight percent, preferably from about 0.5 to about 5 weight percent of, for example, polyvinylpyrrolidone (PVP 30) sold by GAF Corporation, a quaternary conditioner such as a polymer of hydroxyethylcellulose reacted with epichlorohydrin and quaternized with trimethylamine i.e., Polymer JR 400 sold by Union Carbide Corporation and an anti-static conditioner with 5 percent propylene glycol as a stabilizer such as oleyldimethyl benzyl ammonium chloride, sold under the tradename AMMONYX KP, by Onyx Chemicals. The thermal styling lotion can additionally include perfuming agents and the like.

In the case of hair having initially slight to severe moisture deficiency, a supplemental gel conditioner is provided which is applied from one to three times a week or more nightly to further condition and restore the normal moisture content to moisture deficient hair. Such supplemental gel conditioners can contain, in addition to the protein and two humectants, from about 0.1 to about 2.0 weight percent of a water soluble high molecular weight carboxyvinyl polymer, i.e., Carbopol 940 sold by B. F. Goodrich Chemical Company or a similar polymer, from about 20 to about 30 weight percent of denatured ethanol such as 200 proof SD alcohol 40 and a non-ionic surfactant such a polyoxyalkylene derivative of sorbitan monolaurate, the aforementioned TWEEN 20 sold by ICI United States, Inc.

An intensive conditioner for damaged hair is also provided by this invention. The intensive conditioner is used once or twice a month in hair initially having a slight to moderate moisture deficiency and is allowed to remain on the hair for 15 minutes per use before rinsing. In the case of initially severely moisture deficient hair, the intensive conditioner is used weekly and allowed to remain on the hair for about 25 minutes. In addition to the two humectants and protein, the intensive conditioner can include various hair conditioners such as an aqueous cationic surface active agent such as cetyltrimethyl ammonium chloride, i.e., BARQUAT CT-429 sold by Lonza, Inc. in an amount of from about 0.5 to about 5 weight percent of the compositions, from about 0.5 to about 5.0 weight percent of an acid stabilized glycerol monostearate, i.e., Lexemul AR sold by Inolex Corporation, from about 0.5 to about 5.0 weight percent of a high molecular weight cetyl alcohol-polyethylene glycol ether complex, i.e., Promulgen D sold by Robinson-Wagner Co., from about 0.5 to about 10 weight percent of mineral oil, preferably 65 to 75 weight, from about 0.5 to about 10 weight percent of isopropyl myristate, from about 0.5 to about 10 weight percent of a thickener such as cetyl alcohol and from about 0.5 to about 10 weight percent of ethylene glycol monostearate, i.e., Product EG-19 sold by Clintwood Chemical Company.

Moderate and severe moisture deficient hair can additionally be benefited by a deep heat treatment conditioner which is applied to the hair once a month in the case of moderate moisture deficiency and once a week in the case of severe moisture deficiency. The deep heat treatment compositions, in addition to the humectants and protein, contain additional conditioners such as Barquat CT-429, generally employed in amounts of from about 0.5 to about 5 weight percent of the compositions, cetyl alcohol polyethylene glycol high molecular weight ether complex such as Promulgen D which generally is present in an amount of from about 0.5 to about 5 weight percent, from about 0.5 to about 10 weight percent of mineral oil, from about 0.5 to about 10 weight percent of isopropyl myristate, from about 0.5 to about 10 weight percent of cetyl alcohol and from about 0.5 to about 10 weight percent of ethylene glycol monostearate.

A moisture conditioner hair spray composition can be formulated by incorporating from about 1 to about 15 percent by weight of a water soluble resin consisting of 60% vinylpyrrolidone-40% vinylacetate copolymer, i.e. PVP/VA-E-635, sold by General Amiline and Film Corporation, and from about 0.05 to about 1.5 percent by weight of a copolymer of dimethyl polysiloxane and a polyoxyalkylene ester such as Silicone Fluid SF-1066 sold by General Electric and from about 40 to about 80 weight percent of alcohol, i.e., SD Alcohol 40.

The preferred proteins are water or alcohol soluble proteins derived from collagenous sources, i.e., those sold by Inolex Corporation under the tradenames Lexein X250 and WSP-A200 Protein.

The following examples illustrate the compositions of this invention.

EXAMPLE 1

MOISTURE STABILIZING SHAMPOO

A moisture stabilizing shampoo composition is formulated using the following ingredients:

| Ingredient | Weight Percent |
| --- | --- |
| Sodium DL-2-pyrrolidone-5-carboxylate (50% aqueous soln.) | 0.10 |
| Glycerin | 0.10 |
| Protein | 0.10 |
| Dynol SAM | 42.000 |
| Ninol 2012 | 1.00 |
| Lauryl dimethylamine oxide | 2.00 |
| Deriphat 160C | 0.10 |
| Water | to 100 percent |

In addition, the above shampoo composition also includes preservatives, chelating agents, coloring agents, perfume and the like. The following example illustrates such a composition.

EXAMPLE 2

MOISTURE STABILIZING SHAMPOO

| Ingredient | Weight Percent |
| --- | --- |
| Sodium DL-2-pyrrolidone-5-carboxylate (50% aqueous soln.) | 0.10 |
| Glycerin | 0.10 |
| Protein | 0.10 |
| Dynol SAM | 42.000 |
| Ninol 2012 | 1.000 |
| Lauryl dimethylamine oxide | 2.000 |
| Deriphat 160C | 0.100 |
| Water | to 100 percent |
| Methyl Parasept | 0.150 |
| Versene Flakes | 0.100 |
| Citric acid | 0.190 |
| Monomethylol dimethyl hydantoin | 0.100 |
| Perfume | 0.300 |
| Coloring agent | 0.015 |
| Ammonium chloride | 0.600 |

EXAMPLE 3

MOISTURE STABILIZING CONDITIONER

A moisture stabilizing conditioner is formulated using the following ingredients:

| Ingredient | Weight Percent |
| --- | --- |
| Sodium DL-2-pyrrolidone-5-carboxylate (50% aqueous soln.) | 0.0 |
| Glycerin | 0.1 |
| Protein | 0.2 |
| Ethoquad 0/12 | 2.5 |
| Carbowax 4000 | 1.5 |
| Stearic acid | 1.5 |
| Glycerol monostearate | 1.5 |
| Cetyl alcohol | 2.5 |
| DL-pantothenyl alcohol | 0.1 |
| Anti-foam agent | 0.2 |
| Preservative | 0.1 |
| Coloring agent | 0.3 |
| Water | to 100 |

EXAMPLE 4

MOISTURE CONTROL SETTING CONDITIONER

A moisture control setting conditioner composition is formulated using the following ingredients:

| Ingredient | Weight Percent |
| --- | --- |
| Sodium DL-2-pyrrolidone-5-carboxylate (50% aqueous soln.) | 0.500 |
| Glycerin | 1.000 |
| Protein | 1.000 |
| GAF Quat 734 (50% of soln.) | 5.000 |
| Adogen 432 CG | 0.125 |
| Ethoquad 0/12 | 0.375 |
| SD Alcohol | 30.000 |
| Tween 20 | 0.500 |
| Water | to 100 |

The setting conditioner can additionally comprise perfuming agents, coloring agents and the like.

EXAMPLE 5

THERMAL STYLING PROTECTIVE LOTION

A blow-dry conditioning and protective lotion composition is formulated with the following ingredients:

| Ingredient | Weight Percent |
| --- | --- |
| Sodium-DL-2-pyrrolidone-5-carboxylate | 0.10 |
| Glycerin | 0.10 |
| Lexein X250 | 1.00 |
| PVP 30 | 1.00 |
| Oleyl dimethylbenzyl ammonium chloride | 0.50 |
| Water | to 100.0 |

The blow-dry composition can additionally include perfuming agents, preservatives and the like.

EXAMPLE 6

SUPPLEMENTAL GEL CONDITIONER

A supplemental gel conditioner which is used to help to restore moisture to moisture deficient hair is formulated using the following ingredients:

| Ingredient | Weight Percent |
| --- | --- |
| Sodium-DL-2-pyrrolidone-5-carboxylate (50% aqueous soln.) | 2.00 |
| Glycerin | 1.50 |
| Lexein X250 (protein) | 0.50 |
| Carbopol 940 | 0.35 |
| SD Alcohol 40 | 25.00 |

| Ingredient | Weight Percent |
| --- | --- |
| Non-ionic surfactant | 0.5 |
| Perfuming agent | 0.1 |

EXAMPLE 7

DEEP HEAT TREATMENT CONDITIONER

A deep heat treatment conditioner which is used to help restore moisture to moderate to severe moisture deficient hair is formulated using the following ingredients.

| Ingredient | Weight Percent |
| --- | --- |
| Sodium-DL-2-pyrrolidone-5-carboxylate (50% aqueous soln.) | 5.0 |
| Glycerin | 5.0 |
| Protein | 2.5 |
| Barquat CT-429 | 4.3 |
| DL-pantothenyl alcohol | 0.1 |
| Acid stabilized glycerol monostearate | 1.0 |
| Promulgen D | 1.0 |
| Mineral oil 65/75 | 2.0 |
| Isopropyl myristate | 2.0 |
| Cetyl alcohol | 3.5 |
| Ethylene glycol monostearate | 2.0 |
| Perfume | 0.4 |
| Coloring | 0.2 |
| Water | to 100.0 |

The deep heat treatment composition is used once a month on hair having a slight to moderate moisture deficiency and every week on hair which is severely moisture deficient.

EXAMPLE 8

INTENSIVE CONDITIONER FOR DAMAGED HAIR

An intensive conditioner composition is formulated using the following ingredients:

| Ingredient | Weight Percent |
| --- | --- |
| Sodium-DL-2-pyrrolidone-5-carboxylate (50% aqueous soln.) | 4.00 |
| Glycerin | 3.00 |
| Protein | 4.00 |
| Barquat CT-429 | 4.3 |
| Acid stabilized glycerol monostearate | 1.0 |
| Promulgen D | 1.0 |
| Mineral oil 65/75 | 2.0 |
| Isopropyl myristate | 2.0 |
| Cetyl alcohol | 3.5 |
| Ethylene glycol monostearate | 2.0 |
| Perfume | 0.4 |
| Preservative | 0.2 |
| Water | to 100 |

EXAMPLE 9

MOISTURE CONTROL HAIR SPRAY COMPOSITION

A moisture control hair spray composition is formulated from the following ingredients:

| Ingredients | Weight Percent |
| --- | --- |
| Sodium-DL-2-pyrrolidone-5-carboxylate (50% aqueous soln.) | 0.1 |
| Glycerin | 0.1 |
| Alcohol soluble protein | 0.1 |
| PVP/VA-E-635 (50%) | 10.0 |
| Silicone Fluid SF-1066 | 0.2 |
| Citric acid | 0.3 |
| Perfume | 0.3 |
| SD Alcohol 40 | 78.6 |
| Water | to 100.0 |

While all types of hair will benefit from the use of the moisture stabilizing shampoo of this invention, it is preferable to use the compositions in a specific sequence depending upon the state of the hair. For example, in the case of hair initially having a normal moisture content, the hair is shampooed with a moisture stabilizing shampoo in accordance with this invention, the freshly shampooed hair is conditioned by applying a moisture stabilizing conditioner to the freshly shampooed hair, distributing the conditioner throughout the hair and then rinsing the conditioner from the hair. Thereafter, the appropriate moisture control styling lotion, either the setting conditioner if the hair is to be set on, for example, rollers or the thermal styling protective composition if the hair is to be blown dry. If hair spray is used, it is preferred to use the moisture control hair spray in accordance with this invention.

For hair initially having a moisture deficiency, depending upon the severity of the deficiency, the supplemental conditioning gel can be applied to the hair before bedtime at least once a week and, in case of severely moisture deficient hair at least 3 times a week. In addition, moderately moisture deficient hair can be additionally benefited by the application of the intensive conditioner of this invention once or twice a month for about 15 minutes each and severely deficient hair is benefited by the use of the conditioner of Example 8 once a week for about 25 minutes.

In addition, moderately and severely deficient hair can be additionally benefited by the use of the deep heat treatment composition of Example 7, which is applied once a month to hair having a slight to moderate moisture deficiency and once a week to hair which is severely moisture deficient. The use of such deep heat treatment compositions is well-known in the art as is the use of the other compositions embodied within the scope of this invention.

It is to be understood that the foregoing examples are intended to be merely illustrative and that modifications and variations will be apparent to those skilled in the art.

I claim:

1. An aqueous hair treatment composition for restoring and maintaining the proper moisture level in hair comprising from about 0.01 to about 1 weight percent of sodium-2-pyrrolidone-5-carboxylate, from about 0.1 to about 5.0 weight percent of glycerin and from about 0.1 to about 5.0 weight percent of protein derived from a collagenous source, said protein being soluble in at least one liquid of the group consisting of water and ethanol.

2. A composition in accordance with claim 1, wherein said composition is a moisture stabilizing shampoo additionally comprising from about 5 to about 50 weight percent of a detergent comprising sodium lauryl sulfate.

3. The composition of claim 2 additionally comprising from about 0.05 to about 10.0 weight of an amphoteric surface active agent.

4. A composition in accordance of claim 1, wherein said composition is a moisture stabilizing conditioner containing from about 0.5 to 5.0 weight percent of a quaternary ammonium salt conditioner.

5. The composition of claim 4 additionally comprising from about 0.5 to about 5.0 weight percent of a non-cationic conditioner.

6. A composition of claim 1 wherein said composition is a moisture control thermal setting lotion containing from about 0.2 to about 10 weight percent of polyvinyl pyrrolidone and a quaternary ammonium salt conditioner.

7. A composition of claim 1 wherein said composition is a moisture gain deep heat treatment containing from about 0.5 to about 10 weight percent of mineral oil and from about 0.5 to about 5 weight percent of a cationic surface active agent.

8. A composition of claim 1 wherein said composition is a moisture gain intensive conditioner containing from about 0.5 to about 5 weight percent of a cationic surface active agent and from about 0.5 to about 10 weight percent of an acid stabilized glycerol monostearate.

9. A composition of claim 1 wherein said composition is a moisture stabilizing night supplement conditioner containing from about 0.1 to about 2 weight percent of a high molecular weight carboxyvinyl polymer and a nonionic surfactant.

* * * * *